United States Patent [19]

Ross, Jr.

[11] Patent Number: 4,495,050

[45] Date of Patent: Jan. 22, 1985

[54] TEMPERATURE INSENSITIVE POTENTIOMETRIC ELECTRODE SYSTEM

[76] Inventor: James W. Ross, Jr., 39 Hurlburt St., Cambridge, Mass. 02138

[21] Appl. No.: 466,856

[22] Filed: Feb. 16, 1983

Related U.S. Application Data

[63] Continuation-in-part of Ser. No. 211,351, Nov. 28, 1980, abandoned.

[51] Int. Cl.$^3$ ............................................. G01N 27/30
[52] U.S. Cl. .................................... 204/408; 204/416; 204/435
[58] Field of Search ............... 204/408, 416, 417, 418, 204/419, 420, 435

[56] References Cited

U.S. PATENT DOCUMENTS

| | | |
|---|---|---|
| 3,405,048 | 10/1968 | Soltz . |
| 3,445,363 | 5/1969 | Simon et al. . |
| 3,666,651 | 5/1972 | Makabe . |
| 3,707,455 | 12/1972 | Derr et al. . |
| 3,709,796 | 1/1973 | King et al. ........................ 204/1 T |
| 3,730,868 | 5/1973 | Niedrach . |
| 3,926,764 | 12/1975 | Ruzicka et al. . |
| 4,214,968 | 7/1980 | Battaglia et al. . |

FOREIGN PATENT DOCUMENTS 176120 10/1965 U.S.S.R. ............................. 204/420

OTHER PUBLICATIONS

Klaus J. Vetter, "Elektrochemische Kinetik", pp. 370–375, (1961).
Heinz Ebert, "Elektrochemie" pp. 84–95.
Research Disclosure, No. 161, pp. 28–39, Sep. 1977.
Donald T. Sawyer et al., "Experimental Electro-Chemistry for Chemists", p. 57, (1974).

Primary Examiner—G. L. Kaplan

[57] ABSTRACT

A potentiometric electrode having an ion selective half cell containing a non-reactive lead such as platinum in contact with an electrolyte containing a reversible redox couple having a large exchange current and a substantially flat temperature coefficient of potential such as 5 molar iodide, $3 \times 10^{-2}$ molar triiodide, thereby having an electrode with a rapid and reproducible temperature response.

7 Claims, 8 Drawing Figures

TEMPERATURE INSENSITIVE POTENTIOMETRIC ELECTRODE SYSTEM

This application is a continuation-in-part of Ser. No. 211,351, filed on Nov. 28, 1980 and now abandoned.

SUMMARY OF INVENTION

This invention relates to electrochemical detection and measurement, and more particularly to potentiometric systems for selectively detecting and measuring ion activity in solution, and electrodes having an improved response time to changes in temperature of the solution containg the ion.

Broadly, a potentiometric ion-selective electrode is a half cell which includes an ion-selective membrane, at least a portion of one surface of which is intended to contact physically the solution in which the activity of the particular ionic species is to be detected and/or measured. At least a portion of the other surface of the membrane is electrically coupled to an electrically conductive lead intended to be connected in turn to the input of a high input impedance detector or electrometer. In the electrodes of interest to the present invention, the electrical coupling of the membrane to the lead is through an internal ionic solution which contains a fixed concentration or activity of the ionic species of interest. The lead is coupled to the internal solution typically through an Ag/AgCl or calomel reference electrode in order to provide a stable, well-defined internal contact potential. When the electrode is placed in contact with the sample system, an ionic charge transfer across the membrane sets up an electrical potential. One can complete the system by contacting the same sample solution with another half cell or potentiometric reference electrode which provides a fixed potential. The sum of the potentials from the two half cells can be determined by connecting them in series to one another and to an electrometer.

The membranes of such potentiometric ion-selective electrodes comprise either solid or liquid ion-exchangers or neutral sequestering agents and are as diverse as the well known glass membranes which are respectively selective, for example, to $H^+$, $Na^+$, $K^+$ and the like, crystalline membranes such as $LaF_3$ which is selective to $F^-$, and liquid materials such as dodecylphosphoric acid or an antibiotic such as trinactin held in a porous, inert, solid matrix.

In accordance with the well-known Nernst equation, the relationship between the potential E measured by the electrometer and the activity $A_s$ of the ionic species of interest, is log-linear usually over several orders of magnitude of ionic activity (e.g. from above about 1M to below about $10^{-5}$M for fluoride ion measured with a LaF electrode. The slope of this log-linear relationship is given by the Nernst factor and therefore changes with temperature. Theoretically, all of the log-linear relationships for various temperatures for a given electrode will intersect at a single point known as the isopotential point. Ideally, commercial pH electrodes are designed so that the isopotential point is close to pH7, and the temperature compensating circuits in commercial instrumentation are designed with this in mind.

Real electrodes, however, whether ion-sensitive or reference, do not behave exactly as predicted by theory, and the various response curves, instead of intersecting at a point, tend to cross within a rather diffuse area. The reason can be ascertained by examining the Nernst equation for the cell potential:

$$E = k + RT/f \log (A_s + \text{samp})/(A_s + \text{int}) \qquad (1)$$

wherein, as well known, k is a constant, RT/f is the Nernst factor (normally having a value of 59.16 mv at 25° C.), ($A_s$+samp) is the activity of the ionic species of interest in the sample solution, and ($A_s$+int) is the activity of the ionic species of interest in the internal filling solution. These deviations from ideal behavior arise from two sources: The time required to achieve temperature equilibrium, and the non-linearity of the temperature/EMF characteristics of the electrodes.

In equation (1), the second term $RT/f \log (A_s+\text{samp})/(A_s+\text{int})$ is the potential due to the ion-selective membrane. The first term, k, is the sum of all other sources of potential in the cell, including the external reference electrode potential, the internal reference electrode potential, the liquid junction potential and thermal potentials within solutions contacting the reference elements. Theoretical potential/activity curves for various temperatures will therefore intersect at a true isopotential point only if the sum of all the potentials in the k term is a linear function of temperature and the term ($A_s$+int) is temperature invariant. Clearly, in conventional systems, these conditions are not fulfilled.

With regard to the problem of temperature equilibrium, when a pair of potentiometric electrodes forming a measuring cell is suddenly exposed to the sample solution at a new temperature, considerable time is required for all of the component parts of the electrodes to reach the new temperature. This time varies with electrode design, ambient temperature and the temperature differential. For a typical commercial combination pH electrode subjected for example to a 10° to 20° C. temperature change, from about five to ten minutes may be required before internal temperature gradients are reduced to the range of a few tenths of a degree or less. During the period required to reach temperature equilibrium, the measured potential will drift. The problem is exacerbated by the use of reference electrodes both for the external reference and within the ion-selective electrode, both of which reference electrodes require the saturation of a sparingly soluble salt (e.g. Ag/AgCl). Such reference electrodes exhibit "temperature hysteresis" since due to the slow rates of solution and precipitation of the sparingly soluble salt, considerable time is required to achieve chemical equilibrium beyond that required to establish the new temperature. This slow chemical equilibration with temperature change is the chief factor contributing to electrode drift, and hence is the limiting process which determines accuracy of measurement and the need for frequent restandardization.

If one waits long enough (as long in some instances as hours or days) both chemical and temperature equilibrium can be established in the present commercial electrodes, and reproducible reliable data can be obtained, but clearly this situation has little utility for real-time measurement or process control.

Simon et al, in U.S. Pat. No. 3,445,363, issued May 20, 1969, recognized the desirability of an electrode assembly in which all the isotherms would intersect at the same point, preferably around pH7 and at the electrical zero of the cell potential. To this end, Simon et al teach adding to the internal electrolyte of the assembly, a buffer comprising a solvent such as water, glycerol or the like, a mono or polybasic acid such as p-nitropenol, a mono or polyacidic base such as morpholine, and a source of at least one of the species of ions which determines the potential of the internal reference electrode in contact with the buffer. The internal reference electrode to which Simon et al refer is the usual metal/metal salt electrode such as the Ag/AgCl or the $Hg/Hg_2Cl_2$ electrodes.

Accordingly, the principal object of the present invention is to provide means for and a method of forming a potentiometric system for sensing ions in solution, in which system the electrodes per se are temperature-compensated. Another object of the present invention is to provide a potentiometric electrode for sensing ions in solution, in which electrode thermal and chemical equilibria can be established much more rapidly than is possible with the type of electrode currently in use. Still other objects of the present invention are to provide such potentiometric electrodes which yield, over a wide range of activities and temperatures, an ion-activity response which is substantially temperature insensitive; to provide such electrodes which can be calibrated by the manufacturer and used with electrometric devices which do not require temperature compensation circuits; to provide such electrodes in which the response is fast and stable at a submillivolt level for very extended periods of time; and to provide a substantially temperature-insensitive potentiometric membrane electrode which is simple and inexpensive to manufacture.

Other objects of the present invention will in part be obvious and will in part appear hereinafter. The invention accordingly comprises the apparatus possessing the construction, combination of elements and arrangement of parts, and the processes involving the several steps and the relation and order of one or more of such steps with respect to the others, all of which are exemplified in the following disclosure, and the scope of the application of which will be indicated in the claims.

BRIEF DESCRIPTION OF THE DRAWINGS

The invention will be better understood and the objects other than those set forth above will become apparent when consideration is given to the following detailed description thereof. Such description makes reference to the annexed drawings wherein.

DETAILED DESCRIPTION OF THE INVENTION

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention generally involves a novel potentiometric electrode for use with an external sample solution having an ionic species of interest, which electrode includes an enclosure having an internal, electrolytic filling electrically coupled to a lead provided for connecting the electrode externally, for example to an electrometer. The electrolyte is preferably nonreactive with the sample solution and in the present invention contains a thermodynamically reversible redox couple having a large exchange current. The lead is an electrically conductive material in direct physical contact with the electrolyte and substantially chemically inert to the latter. The term "potentiometric electrode" as used herein is intended to include all such electrodes used in electrochemical measurement, and specifically includes both ion-sensitive electrodes and reference electrodes. The term "redox couple" as used herein is intended to mean an electrolyte containing both oxidized and reduced stages originating from different valence stages of a given element or combination of elements, the stages being thermodynamically reversible, i.e., each stage being convertible into the other by an infinitesimally small change of potential from some equilibrium value, an inert metal in contact with the electrolyte acquiring a definite and reproducible potential dependent upon the ratio of the two stages present. The term exchange current means the current flow between the stages of the couple and its magnitude is a measure of the speed of attaining the new equilibrium point.

Figure 1:
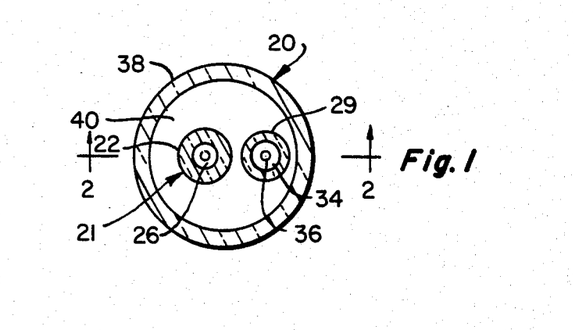
FIG. 1 is a schematic cross-sectional view of a novel electrochemical cell embodying the principles of the present invention.
Figure 2:
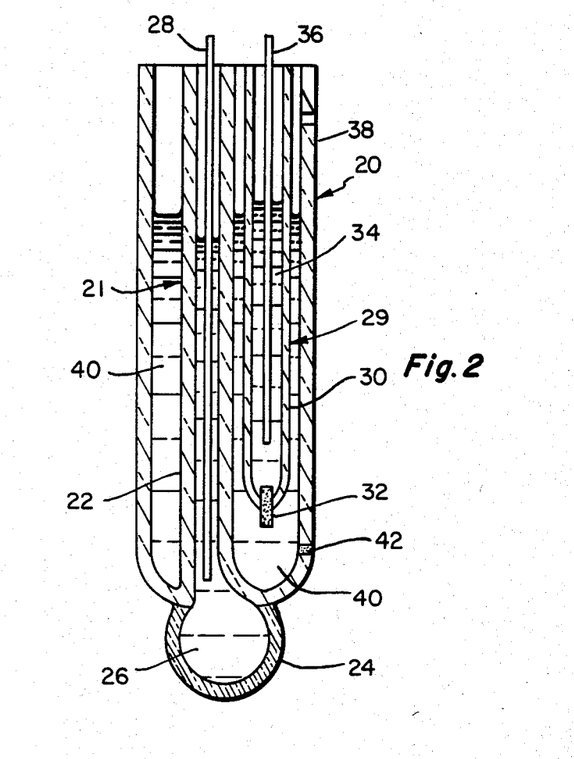
FIG. 2 is a schematic longitudinal cross-section taken along the line 2—2 in the embodiment of FIG. 1.

Referring now the the drawings, there is shown particularly in FIGS. 1 and 2, potentiometric electrode assembly 20 embodying the principles of the present invention. Assembly 20 comprises a novel half-cell 21 including a first enclosure means in the form of elongated, hollow tubular container 22, typically formed of a liquid-impervious, substantially rigid, electrically insulating material such as many well-known high molecular weight polymers, glass or the like, substantially chemically inert with respect to the electrolyte intended to be disposed therein, as will be described later.

One end of container 22 is sealed with a membrane, typically in the form of bulb 24 formed of an ion-sensitive material. For purposes of exposition in the description of the embodiments of FIGS. 1 and 2, bulb 24 will be considered to be a pH membrane, but it will be recognized that bulb 24 can be formed of a large variety of known materials each providing a specific ion-sensitivity. Preferred dimensions, shape and strength of bulb 24 are well-known in the prior art and of course depend on the nature of the particular material from which the membrane is formed. The sealing of the membrane to the end of container 22 likewise depends on the nature of the material and upon techniques for effecting sealing, all well-known in the prior art.

Also, as is well-known in the prior art, such potentiometric electrodes typically include an internal, ionically-conductive filling or electrolyte, which is electrically coupled to an external lead. To this end, electrode 20 includes a body of electrolytic material 26 within container 22, which electrolyte, for purposes of the present invention is simply formed of a phosphate buffer (e.g. a solution containing 0.05M $NaH_2PO_4$ and 0.05M $Na_2HPO_4$) to fix the activity of hydrogen ion, i.e., the pH, and a selected redox couple which will be described later herein. The electrolyte of course can be a true ionic solution, or a gel, sol or the like. Electrolytic material 26 is in direct physical and electrical contact with at least one end of lead 28.

As well-known in the art, the combination of electrolyte 26 and lead 28 is intended to provide means for electrically coupling the electrode to the outside world while maintaining stable internal potentials which arise from the various junctions among the several materials contacting one another within the electrode structure. The structure of the electrode assembly described thus far is quite typical of a prior art ion-sensitive electrode, with of course, the exception of the added redox couple. However, unlike the typical prior art pH electrode assemblies, lead 28 in contact with filling 26 is not a standard internal reference electrode such as the usual Ag/AgCl electrode, but is instead a material which has a high electrical conductivity and which is chemically inert with respect to electrolyte 26. In a preferred embodiment, lead 28 is simply a platinum wire.

Electrolyte 26 in the present invention necessarily includes a redox couple having a relatively large exchange current. This should preferably be $1 \times 10^{-6}$ amp/cm$^2$ or larger. As is well-known, the exchange current is a kinetic property of redox couples, and in effect measures the reversibility of the reversible reaction of the redox couple. Redox couples other than iodide/triiodide which are useful in varying degrees in the present invention are:

It will be recognized that a substantially inert, electrically conductive material/such as platinum and like noble metals, in contact with a solution containing both the oxidized and reduced forms of the couple will develop a fixed and reproducible contact potential. If the temperature of the solution changes, the equilibrium between the reduced and oxidized forms in the couple will rapidly shift, create a new potential which becomes fixed and reproducible concurrently with the attainment of a new equilibrium. Since none of the material of the lead has to be dissolved or precipitated, the change in potential value occurs very rapidly, i.e. in a matter of seconds or less. Preferably, the redox solution has a very small temperature coefficient of redox potential so that the problem of slow attainment of temperature equilibrium is overcome. For example, a useful solution exists using the iodide/triiodide couple at approriate levels of $I^-$ and $I_3^-$, e.g., $I^-$ at a concentration of 5.68M and $I_3^-$ at a concentration of $3.6 \times 10^{-2}$M. Using such a system, changes in the temperature of the components of the electrode assembly, including the internal electrolyte, or changes in the temperature of the solution being measured do not quickly affect the potentials contributed to the cell potential by the filling and lead, and thus accurate and reproducible cell potentials can be measured even before temperature equilibrium is obtained.

The electrode assembly embodying the present invention is illustrated in FIGS. 1 and 2 as a combination electrode or full cell, formed of two half-cells. Half-cell 21, which has thus far been described, essentially can be represented by the following example:

The other half cell, 29, which is a reference electrode, can be represented by the following example:

It will be recognized that the latter string is a condensed description of a novel potentiometric reference electrode incorporating the principles of the present invention and which is shown in FIGS. 1 and 2 as comprising a second enclosure means in the form of an elongated hollow tubular container 30, typically formed of a liquid-impervious, substantially rigid, electrically insulating material, preferably the same material used to form container 22. Container 30 is perforated at one end by a known restrained flow junction 32 shown as a fiber wick, but which as well known in the art, can be a porous frit, a leaky seal, a porous polymer or the like. Also as well known, junction 32 is intended to provide a free diffusion path for fluid flow between the interior and exterior of container 30. Disposed in container 30 is an ionically-conductive filling or electrolyte 34 which typically can be a number of any filling solutions such as 3.5M KCl, intended to constitute a source of ions to provide conductivity, and necessarily containing a selected thermodynamically reversible redox couple with the requisite exchange current. Preferably the latter couple is the same couple used in electrolyte 26. Inasmuch as half-cell 29 is simply a reference electrode, no buffer is needed in the electrolyte.

Lastly, half-cell 29 includes an electrically conductive lead chemically inert to electrolyte 34, shown in the form of platinum wire 36 in physical contact with electrolyte 34.

For convenience, it may be desirable to incorporate both half-cells 21 and 29 into a unitary structure, although it is not necessary for purposes of the present invention. To this end, as shown in FIGS. 1 and 2, a third envelope, 38, is provided surrounding containers 22 and 30 and preferably sealed to container 22 circumferentially about the latter just above the seal between container 22 and membrane 24. Envelope 38 is also preferably filled with electrolyte 40, typically simply a 3.5M KCl solution compatible with electrolyte 34, and from which diffusion can occur through junction 32 with regard to electrolyte 34. In order to complete the cell and provide an ionically-conductive pathway between half-cell 29 and a sample solution in contact with the exterior of bulb 24, a second bridge or restrained flow junction 42, in the form of a minute perforation, is provided in one wall of envelope 38, preferably closely adjacent membrane 24.

EXAMPLE

A specific pH electrode embodying the principles of this invention includes an ion selective half cell having an internal lead of platinum and an internal filling electrolyte having a redox couple comprising 4 molar potassium iodide (KI) and 0.0067 molar iodine ($I_2$) in water ($H_2O$), and a buffer of 0.02 molar boric acid ($H_3BO_3$) adjusted to 7.15 pH with potassium hydroxide (KOH). The reference half cell has the same lead and electrolyte, although the buffer may be omitted.

Figure 3:
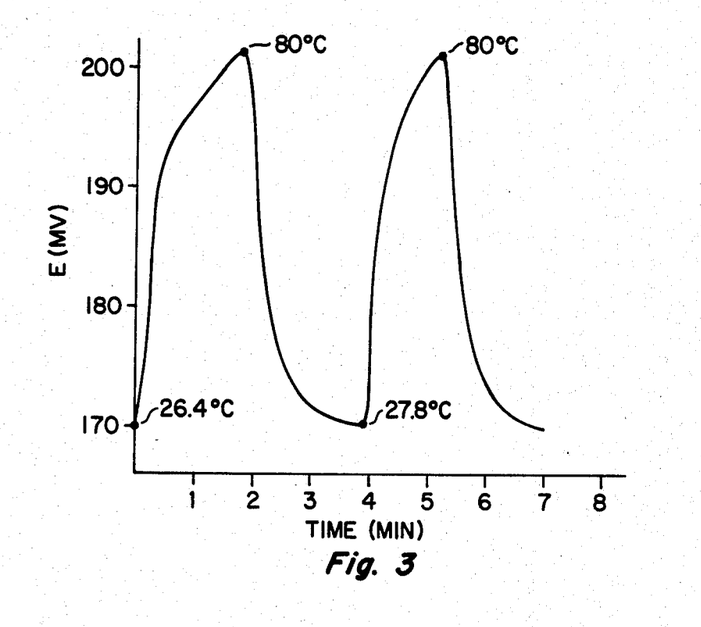
FIG. 3 is an idealized graph of the voltage/time response to changes in temperature in a typical prior art membrane electrode.

To illustrate the distinctions between the present invention and the prior art, an Orion Research Incorporated Model 91-02 combination pH electrode manufactured by Gebruder Moeller Glasblaseri, Zurich, Switzerland, exemplary of a typical prior art structure, was tested in two portions of a sample solution buffered to pH 4.01. One solution was initially brought to a temperature of 80° C., the other being initially at around 26.4° C. The Moeller combination electrode was cycled between the two samples, with as little time as possible intervening between when it was removed from one sample and placed in the other. The electrode assembly was permitted to remain in a given sample until the output, read on an Orion Model 811 pH meter, a high input impedance electrometer manufactured by Orion Research, Cambridge, Mass., provided a reading which was reproducible. As shown in FIG. 3, time intervals of about one to two minutes were required for the Moeller electrode assembly to yield a substantially reproducible voltage (MV) at either temperature. Slight variations in the successive temperatures of the sample solutions were observed, apparently due to the transfer of heat between the samples and the electrode assembly.

Figure 4:
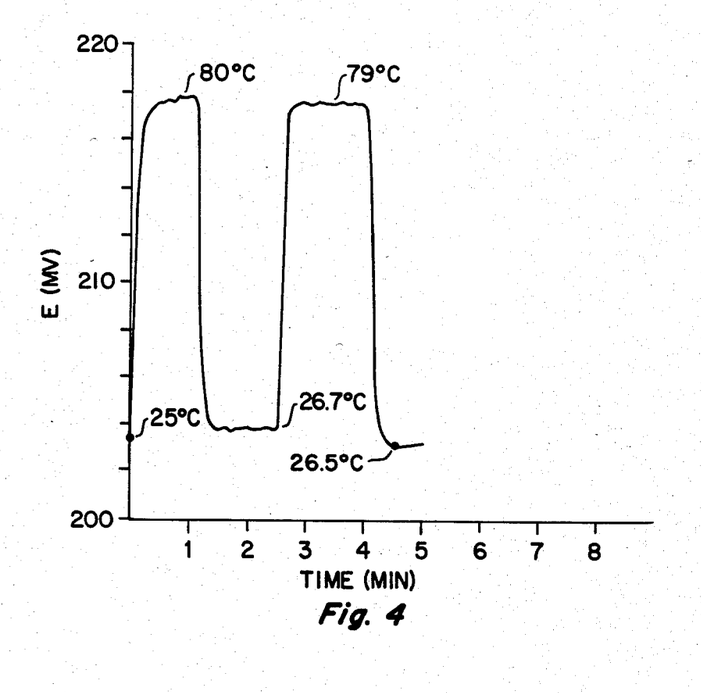
FIG. 4 is a graph of time/voltage response to substantial temperature changes in the cell of the present invention.

An electrode assembly incorporating the principles of the present invention, an Orion Research Incorporated Model 81-02, was made with a pH sensitive membrane and an internal electrolyte formed of a solution of a phosphate buffer containing an iodide/triiodide redox couple. This electrode was subjected to the same procedures in the same samples as the Moeller combination electrode. Upon cycling between samples with initial temperatures of 25° C. and 80° C., as shown in FIG. 4, reproducible potentials indicative of substantial temperature independence were reached in a matter of less than about 30 seconds.

Not only does the provision of redox couple with a chemically inert lead as the internal electrolyte and coupling for the present invention provide a much faster response to temperature changes than the prior art, but of substantial interest with regard to the present invention is the nature of the redox couple temperature coefficient, i.e., the change in contact potential with the metal lead due to equilbrium shifts responsively to ambient temperature. For example, the temperature coefficient of a typical redox couple with a requisitely large exchange current, e.g., iodide/triiodide, was determined for several different ratios of triiodide to idodide at a number of different concentrations of the oxidized and reduced stages. Several curves, shown in FIG. 5, wherein the contact potential (MV) with respect to a platinum wire was graphed on an expanded scale against temperature in degrees C., were obtained experimentally for different values and ratios of iodide and triiodide in an iodide/triiodide couple as follows:

TABLE 1

| Curve | Conc. M ($I^-$) | Conc. M. ($I_3^-$) | Ratio ($I_3^-/(I^-)^3$) |
|---|---|---|---|
| A | 2.84 | $1.835 \times 10^{-2}$ | $8.0 \times 10^{-4}$ |
| B | 2.84 | $8.25 \times 10^{-3}$ | $3.6 \times 10^{-4}$ |
| C | 2.84 | $4.58 \times 10^{-3}$ | $2.0 \times 10^{-4}$ |

TABLE 1-continued

| Curve | Conc. M ($I^-$) | Conc. M. ($I_3^-$) | Ratio ($I_3^-/(I^-)^3$) |
|---|---|---|---|
| D | 2.84 | $1.00 \times 10^{-3}$ | $4.37 \times 10^{-5}$ |

Another curve, E, was obtained for an iodide concentration of 5.68M and a triiodide concentration of $3.67 \times 10^{-2}$M, to provide a ratio of $2 \times 10^{-4}$. This latter illustrates that the temperature coefficient is not fully a function of the ratio, but is also dependent upon the concentration. It is apparent from the curves of FIG. 5 that the slope, shape, and symmetry of the temperature coefficient about the isopotential point at approximately 25° C. for a redox couple can be selected according to the concentration of the stages of the couple and the ratio thereof to one another. This factor becomes important when one remembers that the internal filling electrolyte of the pH electrode or half-cell 21 contains a mixture of the redox couple and a buffer to fix the internal activity of the ion of interest, i.e., $H^+$ in the example given.

The response due to the redox couple, if flat, will lead to a rapid attainment of potential. If the response due to the redox couple and the buffer are not flat, but mirror images, the response will be slower, due to the redox couple curve, but the final response will be that called for by the isopotential condition.

Figure 6:
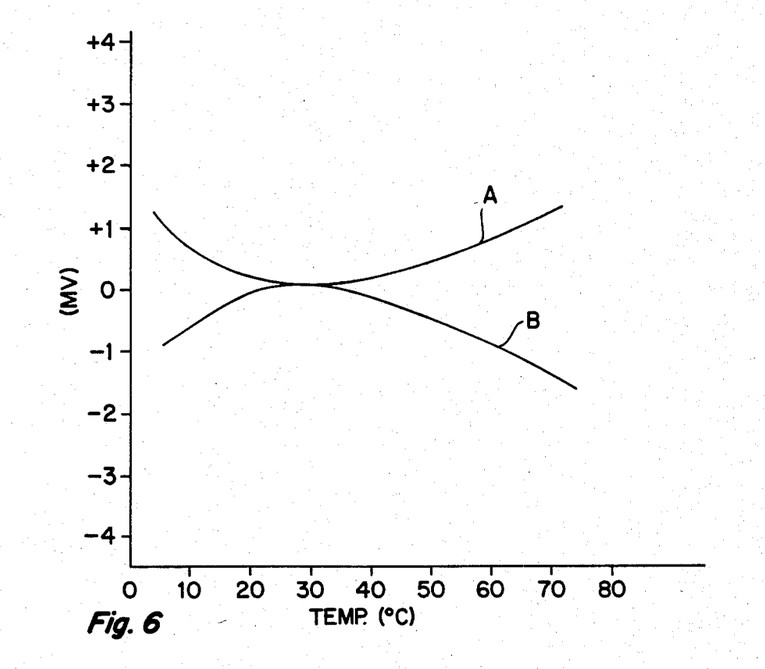
FIG. 6 is a graph of temperature/voltage response of a matched buffer and redox couple.

As shown in FIG. 6, a buffer such as the phosphate buffer used in half-cell 21 itself has a temperature coefficient which is substantially a second degree curve which is upwardly concave, when graphed with an abscissa of temperature values increasing from the left and an ordinate of potential of pH values increasing upwardly. The temperature coefficient curve for a typical buffer has been reproduced as Curve A in FIG. 6. It will also be observed that on the same ordinate and abscissa, a selected redox couple will display a temperature coefficient curve (shown at B) which is concave downwardly such that the two temperature coefficients are substantially inversely related to one another. Consequently, one can provide an electrolyte 24 for a pH or other ion-sensitive electrode employing a buffer to internally fix the activity level of the ion of interest, such that the two temperature coefficients approximately cancel one another out, rendering the electrode substantially temperature invariant.

Figure 7:
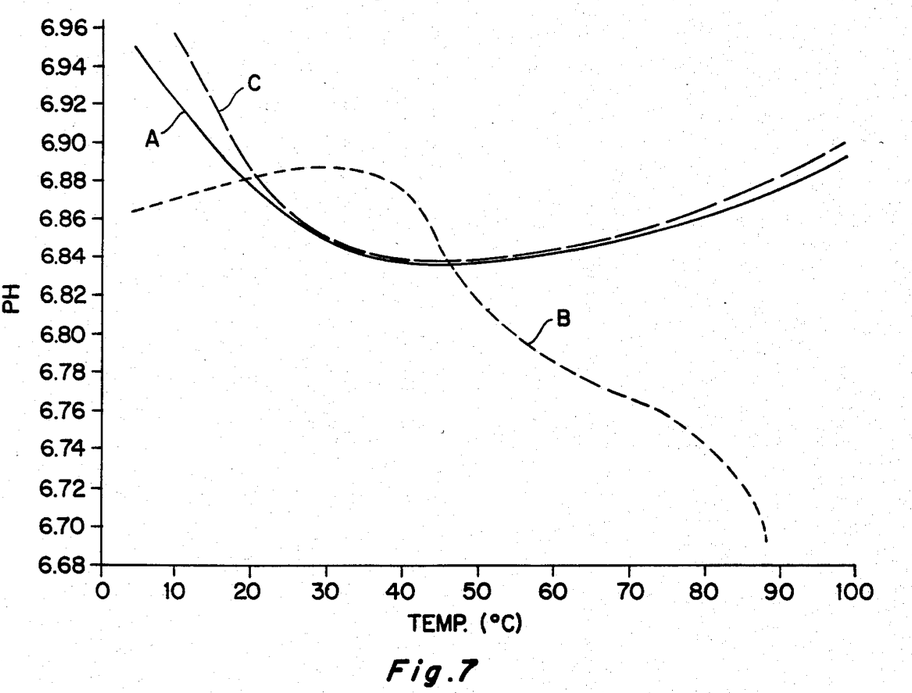
FIG. 7 is a graph of pH/temperature showing the variation therein for a known standard solution and the response thereto for both the electrode assembly of the present invention and a prior art electrode assembly.
Figure 8:
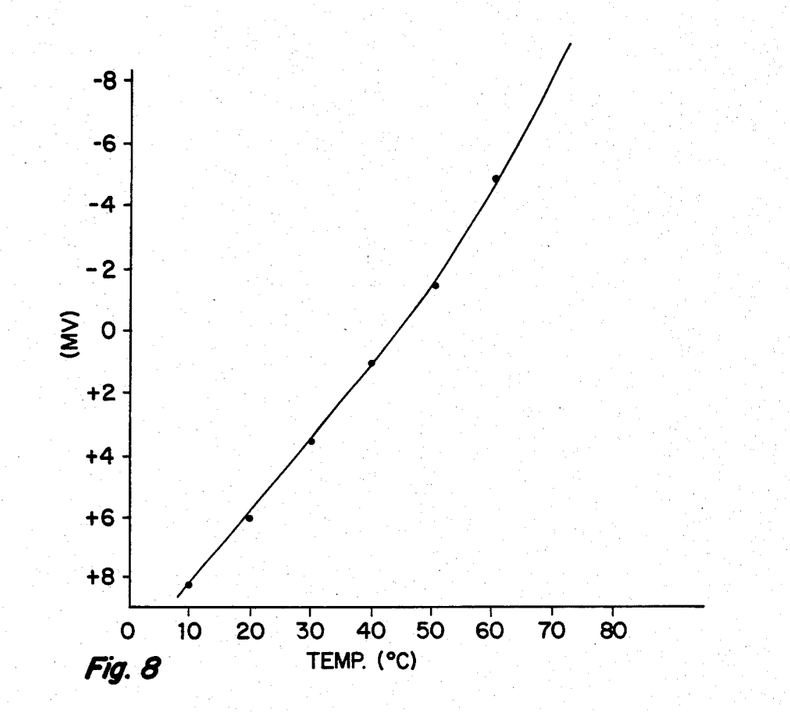
FIG. 8 is a graph showing the termperature coefficient for a redox couple of low exchange current in combination with an exchange current amplifier.

The effect of substantially inversely matching the temperature coefficients of the redox couple and buffer in an ion-sensitive electrode are dramatically illustrated by testing such an electrode against a sample solution. For example, a sample solution was prepared from a National Bureau of Standards phosphate buffer, the true, published temperature coefficient thereof being shown as Curve A in FIG. 7. The pH of this sample solution was determined over a substantial number of temperatures between about 5° and 90° C., using a standard prior art Moeller Model 91-02 pH electrode assembly. The curve of pH measurements obtained from the Moeller electrode on a Model 811 Orion pH meter is shown at B on FIG. 7. The lack of correlation between Curves A and B is not only extremely apparent, but on successive repetitions, Curve B proved to be not very reproducible. On the other hand, using a pH electrode assembly of the present invention in which the internal electrolyte 24 of half-cell 21 was a mixture of buffer and redox couple with substantially inverse temperature coefficients, one obtained Curve C, which on several repetitions proved highly reproducible. The coincidence of Curves A and C illustrates the very substantial difference between the effects of temperature on prior art electrodes and the substantial temperature independence achieved by electrodes incorporating the present invention. The term buffer as used herein means both a hydrogen ion buffer and solution containing a fixed concentration of the ion which the electrode determines.

The nature of the compensating curve obtained by adding the desired redox couple to the internal electrolyte in an electrode is not necessarily limited to the curves obtained from thermodynamically reversible couples having high exchange currents. It has been unexpectedly found that useful and reproducible E/T curves can also be obtained using couples which are not necessarily electrochemically reversible, i.e., have such a low exchange current that an attempted measure of their temperature/potential coefficients cannot ordinarily be made because the measured potentials are unpredictable and unreproducible. This enlarges the number of couples useful for purposes of the present invention, thereby substantially increasing the range of potentials and slopes available for compensation purposes. However, such low exchange current couples may be employed only in conjuction with a high exchange current thermodynamically reversible, chemically compatible redox couple, and under the following conditions:

The two couples must be intimately mixed in a common solution (the high exchange current couple being referred to as the amplifier couple for reasons appearing hereinafter, and the low exchange current being referred to as the principal couple) wherein the relative concentration of the couples is such that the concentration of the principal couple is an order of magnitude or more greater than that of the amplifier couple. The two couples are selected such that the principal couple will react reversibly in a redox reaction with the amplifier couple.

For example, one can use as the principal couple the chlorine/chloride couple described as follows:

the latter characteristically having an exchange current so low that one cannot ordinarily measure such current reliably.

However, a pertinent amplifier couple meeting the requirements above-noted, for example, is the familiar iodine/iodide couple as follows:

These two will rapidly and reversibly react as follows:

At equilibrium, the relative concentration of $Cl_2$ and $Cl^-$ are substantially unchanged because as noted above, a necessary condition is that The amplifier couple, although present in relatively small concentration, thus provides an exchange current which permits one to make the desired measurement of E/T with respect to the combined solution, but because of the very large relative amount of the principal couple present, the values of E will be determined by the latter and not by the amplifier couple. The effect of the principal couple swamps the effect of the amplifier couple on the potential determined.

Figure 5:
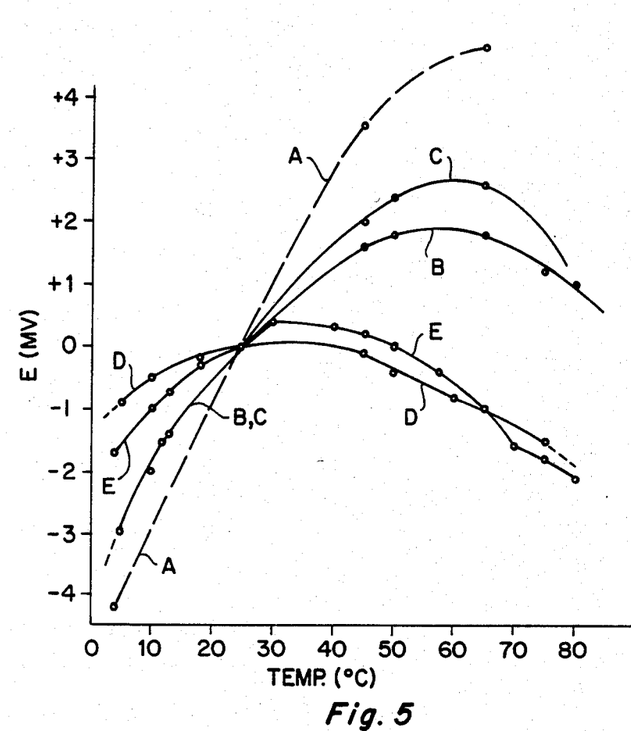
FIG. 5 is a graph showing the temperature coefficient curves for a family of concentrations and ratios for a selected redox couple.

The behavior of the two-couple system was demonstrated by preparing a solution containing 0.1M HCl as a source of chloride ions, adding 25 ppm $Cl_2$ as NaOCl, and providing a small amount of the amplifier couple in the form of $10^{-4}$M $I_2$. The solution was divided into two parts and placed into respective beakers, one of which was held at 25° C., the second being varied in temperature. Platinum electrodes were inserted into each of the beakers and connected as respective inputs to an electrometer. The contents of the two beakers were interconnected through a salt bridge in the form of a tube filled with the solution. The temperature of the second beaker was then progressively varied by increments from a low of about 5° C. to a high of about 75° C. The resulting potentials as a function of temperature as shown in the graph of FIG. 5, illustrating that by use of an amplifier couple, one can obtain a reproducible E/T even from couples with exchange currents ordinarily inadequate to make such measurement.

The present invention has been described with reference to one or more particular embodiments thereof, and it is intended that all matters contained in the above description or shown in the accompanying drawings shall be interpreted in an illustrative and not in a limiting sense since it should be understood that those skilled in the art may make many other modifications and embodiments thereof which will fall within the spirit and scope of the principles of this invention.

What is claimed as new and desired to be secured by Letters Patent of the United States is:

1. A potentiometric electrode measuring system characterized by rapid response and relative insensitivity to temperature changes and having measuring and reference electrodes, each having: an inert electrode lead, and a filling solution including at least a redox couple having
   (i) an exchange current of the order of $10^{-6}$ amperes/cm$^2$ or greater, and
   (ii) a ratio of reduced to oxidized forms of such magnitude as to provide an electrode potential that is invariant with temperature.

2. A potentiometric measuring system according to claim 1 in which said redox couple comprises an $I^-$, $I_3^-$ couple.

3. A potentiometric measuring system according to claim 2 in which said $I^-$ is present in on the order of molar concentrations and said $I_3^-$ is present in on the order of hundreth-molar concentrations.

4. A potentiometric measuring system according to claim 2 in which said measuring electrode includes an ion-selective pH membrane.

5. A potentiometric measuring system according to claim 2 in which the ratio $(I_3^-)/(I^-)^3$ is on the order of from $10^{-4}$ to $10^{-5}$.

6. A potentiometric measuring system according to claim 1 in which said internal filling solution comprises at least an amplifier couple in the form of a thermodynamically reversible redox couple providing an exchange current on the order of $10^{-6}$ amperes per square centimeter or greater, and a principal couple in the form of a thermodynamically irreversible couple having an exchange current at least an order of magnitude less than that of the amplifier couple and present in a concentration of about an order of magnitude or more greater than the concentration of the amplifier couple, said amplifier and principal couples interacting in a redox reaction to provide an exchange current of substantially greater magnitude than provided by the principal couple alone, but an electrode potential determined primarily by the principal couple.

7. An electrode according to claim 6 in which said amplifier couple comprises an iodine/iodide couple and said principal couple comprises a chlorine/chloride couple.

* * * * *